(12) United States Patent
Asmussen et al.

(10) Patent No.: US 8,647,314 B2
(45) Date of Patent: Feb. 11, 2014

(54) GINGIVAL WAFER

(75) Inventors: Bodo Asmussen, Bendorf (DE);
Michael Simon, Boppard-Buchholz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 104 days.

(21) Appl. No.: 12/736,109

(22) PCT Filed: Feb. 27, 2009

(86) PCT No.: PCT/EP2009/001439
§ 371 (c)(1),
(2), (4) Date: Sep. 10, 2010

(87) PCT Pub. No.: WO2009/115178
PCT Pub. Date: Sep. 24, 2009

(65) Prior Publication Data
US 2011/0009834 A1    Jan. 13, 2011

(30) Foreign Application Priority Data

Mar. 15, 2008 (DE) .................. 10 2008 014 533

(51) Int. Cl.
*A61M 35/00* (2006.01)
(52) U.S. Cl.
USPC ........................................... 604/289
(58) Field of Classification Search
USPC ........................................... 604/289
See application file for complete search history.

(56) References Cited

U.S. PATENT DOCUMENTS

| | | | | | |
|---|---|---|---|---|---|
| 4,713,243 | A | * | 12/1987 | Schiraldi et al. | 424/676 |
| RE33,093 | E | * | 10/1989 | Schiraldi et al. | 424/676 |
| 4,900,552 | A | * | 2/1990 | Sanvordeker et al. | 424/422 |
| 5,166,233 | A | * | 11/1992 | Kuroya et al. | 524/37 |
| 5,326,685 | A | * | 7/1994 | Gaglio et al. | 433/215 |
| 5,425,953 | A | * | 6/1995 | Sintov et al. | 424/404 |
| 5,626,866 | A | * | 5/1997 | Ebert et al. | 424/447 |
| 5,707,736 | A | * | 1/1998 | Levy et al. | 428/375 |
| 5,713,738 | A | * | 2/1998 | Yarborough | 433/215 |
| 5,725,879 | A | | 3/1998 | Daoudal | |
| 5,879,691 | A | | 3/1999 | Sagel et al. | |
| 5,894,017 | A | * | 4/1999 | Sagel et al. | 424/401 |
| 5,989,569 | A | * | 11/1999 | Dirksing et al. | 424/401 |
| 6,045,811 | A | | 4/2000 | Dirksing et al. | |
| 6,096,328 | A | * | 8/2000 | Sagel et al. | 424/401 |
| 6,136,297 | A | | 10/2000 | Sagel et al. | |

(Continued)

FOREIGN PATENT DOCUMENTS

EP    0641560    3/1995
JP    S59196814    11/1984

(Continued)

OTHER PUBLICATIONS

List, P.H., et al.; "Hagers Handbuch der pharmaceutischen Praxis"; Springer Verlag, Berlin-Heidelberg, New York, pp. 690-691 (1971).

*Primary Examiner* — Tatyana Zalukaeva
*Assistant Examiner* — Guy K Townsend
(74) *Attorney, Agent, or Firm* — D. Peter Hochberg; Sean F. Mellino; Richard A. Wolf

(57) ABSTRACT

Strip-shaped forms of administration for administering an active ingredient via the mucous membrane of the gums.

13 Claims, 3 Drawing Sheets

(56) References Cited

U.S. PATENT DOCUMENTS

| | | | |
|---|---|---|---|
| 6,155,832 A * | 12/2000 | Wiesel | 433/215 |
| 6,287,120 B1 * | 9/2001 | Wiesel | 433/215 |
| 6,343,932 B1 * | 2/2002 | Wiesel | 433/215 |
| 6,419,906 B1 * | 7/2002 | Xu et al. | 424/53 |
| 6,435,873 B1 * | 8/2002 | Burgio | 433/80 |
| 6,500,408 B2 * | 12/2002 | Chen | 424/53 |
| 6,551,579 B2 * | 4/2003 | Sagel et al. | 424/53 |
| 6,649,147 B1 * | 11/2003 | Ye et al. | 424/49 |
| 6,682,721 B2 * | 1/2004 | Kim et al. | 424/53 |
| 6,685,923 B2 * | 2/2004 | Peterson et al. | 424/53 |
| 6,780,401 B2 * | 8/2004 | Kim et al. | 424/53 |
| 6,884,426 B2 * | 4/2005 | Sagel et al. | 424/401 |
| 6,916,463 B2 * | 7/2005 | Lee et al. | 424/53 |
| 6,946,142 B2 * | 9/2005 | Chang et al. | 424/435 |
| 6,949,240 B2 * | 9/2005 | Sagel et al. | 424/53 |
| 6,997,708 B2 * | 2/2006 | Allred et al. | 433/80 |
| 7,018,622 B2 * | 3/2006 | Goodhart et al. | 424/49 |
| 7,074,042 B2 * | 7/2006 | Allred et al. | 433/216 |
| 7,122,199 B2 * | 10/2006 | Sagel et al. | 424/401 |
| 7,247,022 B2 * | 7/2007 | Allred et al. | 433/216 |
| 7,264,471 B2 * | 9/2007 | Malcmacher et al. | 433/215 |
| RE42,126 E * | 2/2011 | Ye et al. | 424/49 |
| 2005/0063918 A1 * | 3/2005 | Charmot et al. | 424/48 |
| 2005/0063919 A1 * | 3/2005 | Chang et al. | 424/48 |
| 2005/0063920 A1 * | 3/2005 | Chang et al. | 424/48 |
| 2005/0063921 A1 * | 3/2005 | Charmot et al. | 424/48 |
| 2005/0129763 A1 | 6/2005 | Sowden | |
| 2005/0137109 A1 * | 6/2005 | Quan et al. | 510/303 |
| 2005/0260544 A1 | 11/2005 | Jones et al. | |
| 2006/0292520 A1 | 12/2006 | Dillon et al. | |
| 2007/0092454 A1 * | 4/2007 | Cameron et al. | 424/49 |
| 2007/0207192 A1 | 9/2007 | Holl et al. | |
| 2007/0207207 A1 * | 9/2007 | Tzannis et al. | 424/464 |
| 2007/0218114 A1 * | 9/2007 | Duggan et al. | 424/443 |
| 2007/0259011 A1 * | 11/2007 | Sagel et al. | 424/401 |
| 2008/0233055 A1 * | 9/2008 | Fisher et al. | 424/49 |
| 2009/0092643 A1 * | 4/2009 | De Vreese et al. | 424/401 |

FOREIGN PATENT DOCUMENTS

| | | |
|---|---|---|
| JP | H05506655 | 9/1993 |
| JP | 2001335470 | 12/2001 |
| JP | 2002114677 | 4/2002 |
| JP | 2004538085 | 12/2004 |
| JP | 2007502823 | 2/2007 |
| WO | 9116041 | 10/1991 |
| WO | WO 95/09608 | 4/1995 |

\* cited by examiner

GINGIVAL WAFER

CROSS-REFERENCE TO RELATED APPLICATIONS

This application is a National Stage application of International Application No. PCT/EP2009/001439, filed on Feb. 27, 2009, which claims priority of German application number 10 2008 014 533.5, filed on Mar. 15, 2008, both of which are incorporated herein by reference in their entireties.

BACKGROUND OF THE INVENTION

1. Field of the Invention

The present invention relates to strip-shaped forms of administration, or administration forms, for administering an active ingredient via the mucous membrane of the gums.

2. Description of the Prior Art

Strip-shaped products for application in the mouth are sold in the cosmetic field as dental care products. There are, for example, tooth-whitening strips available on the market that are provided with a tooth-bleaching composition and are placed on the teeth to achieve a long-lasting contact between the teeth and the bleaching composition. Such tooth-whitening strips are described, for example, in the patent specifications U.S. Pat. No. 5,879,691, U.S. Pat. No. 6,045,811 and U.S. Pat. No. 6,136,297, as well as in the published application US 2006/0292520 A1.

Strip-shaped products for oral administration of active pharmaceutical ingredients are available in the form of forms of administration that disintegrate in the mouth. These strip-shaped forms of administration are usually designated as "thin oral strips" or "wafers". Products of this type that are already being marketed are the products soled under the trade marks TRIAMINIC®, THERAFLU®, GAS-X® or BENADRYL®, for example. These products are pharmaceutical preparations that are designed such that the form of administration quickly disintegrates in the mouth. Their rapid disintegration is meant to facilitate swallowing the active pharmaceutical ingredient contained therein. After swallowing, the active pharmaceutical ingredient is absorbed in the gastrointestinal tract. The active pharmaceutical ingredient administered with these commercially available strip-shaped forms of administration is therefore subject to the "first pass" metabolism.

One possibility of avoiding the "first pass" metabolism is the absorption of active pharmaceutical ingredients directly via the mucous membranes. The blood circulation through the mucous membranes takes place via a network of capillaries that allow direct access of the active ingredient to the systemic blood circulation. It is thereby possible to avoid the "first pass" metabolism by diffusion of an active ingredient into the capillary network of the oral mucosa. To achieve this, the active ingredient must be prevented from being swallowed prematurely and its absorption in the oral cavity via the mucous membrane has to be enhanced.

The lips, the cheeks, the hard and the soft palate, the tongue and the floor of the mouth define the oral cavity. Since the mucous membranes of the oral cavity are readily accessible, the oral cavity is a site especially suited for a transmucosal administration of active ingredients. The oral mucous membranes include the sublingual mucosa, the buccal mucous membranes, the mucosa of the gums, the mucous membranes of the palates, as well as the mucous membranes of the lips. The specific site of application in the oral cavity can have an effect on the bioavailability of an active ingredient. In the oral cavity, the transmucosal absorption of active ingredients predominantly takes place via the non-keratinised mucous membranes, above all in the region of the cheeks and below the tongue. However, active ingredients can also be absorbed via the keratinised tissue of the gums. Choosing the gums as the application site affords three major advantages: (A) a very strong blood circulation, so that there is a good access to the systemic blood circulation, (B) a low mechanical stress acting on a form of administration applied there, e.g. chewing movements, (C) only little saliva flowing around the form of administration so that a reduced portion of active pharmaceutical ingredient is swallowed.

An important factor influencing the bioavailability is the contact time between the absorptive epithelial tissue and the active pharmaceutical substance. In principle, a partial absorption can also take place in a rapidly disintegrating form of administration, it is true, but only on condition that the active ingredient has favourable physicochemical properties in terms of transmucosal absorption, e.g. low molecular weight, lipophilic character, etc. For the majority of the active ingredients, particularly peptide agents, for which a transmucosal administration would be advantageous, a prolonged contact time with the absorptive mucous membrane surface is of crucial importance to enable the active ingredient to be absorbed in an amount necessary for achieving the therapeutic effect.

What is available on the market for administering active ingredients via the oral mucous membranes, besides spraying solutions, are above all various tablet formulations. There are sublingual tablets, e.g. NICORETTE® microtabs, which contain nicotine, or UPRIMA® tablets, which contain apomorphine as active ingredient. In addition, there are buccal tablets, e.g. FENTORA®, which contain fentanyl, or BUCCASTEM®, which contain prochlorperazine as active ingredient. Such tablets, however, do have some disadvantages, including (A) an unpleasant mouthfeel, since they cause a sensation of having a foreign body under the tongue, (B) variability in the extent of absorption, and (C) the risk of a complete tablet being swallowed cannot be excluded.

To avoid or at least ameliorate these disadvantages, it would be desirable to have a dosage form by which an active ingredient can be reliably administered via a mucous membrane in the oral cavity, the dosage form being applied at a site in the mouth that does not encumber the patient and where it can be worn even for a prolonged period of time. In addition, it would be advantageous if the dosage form were adapted such that only a correct positioning, and one that is self-explanatory to the user, will be possible in order to avoid application errors.

SUMMARY OF THE PRESENT INVENTION

This object is achieved with the present invention in a surprisingly simple manner by providing a strip-shaped form of administration for application in the oral cavity, particularly for covering an area of the outer gums. The forms of administration according to the present invention enable a close contact with the mucous membrane of the gums and a long retention time on the absorptive tissue, thereby enhancing the transmucosal absorption of an active ingredient through the mucous membrane of the gums.

The subject matter of the present invention is strip-shaped forms of administration for the transmucosal administration of an active ingredient via the gums, comprising a strip of material and at least one active ingredient.

The strip-shaped forms of administration according to the invention have a notch in the edge of one of the two longitudinal sides of the strip of material. In the forms of administration according to the invention, the notch is usually arranged in the middle of the longitudinal edge. The notch may, however, also be arranged nearer towards one of the ends of the strip of material. This notch is a cut-out in the strip of material through which passes the frenulum of the upper lip (Frenulum labii superioris) or the frenulum of the lower lip (Frenulum labii inferioris) when the form of administration is being used. The frenula are thin folds of connective tissue covered with oral mucosa and projecting into the vestibule of the mouth and which extend in the median plane of the mouth from the inside of the lip toward the gingiva of the alveolar process. The frenulum of the upper lip is more distinct than the frenulum of the lower lip. The notch in the strip of material of the form of administration according to the invention thus ensures that the form of administration of the invention is correctly positioned on the gums. The pharmacokinetic reproducibility, safety of application, and patient compliance, in particular for medicaments that need to be administered long-term, is thereby considerably improved.

DETAILED DESCRIPTION OF THE PRESENT INVENTION

In the following, the forms of administration, or administration forms, according to the present invention will be described in more detail with reference to the figures. The figures serve to illustrate the invention by way of example only and do not in any way limit the scope of the invention.

The forms of administration, or administration forms, (1) according to the present invention or, respectively, the strips of material of the strip-shaped forms of administration according to the present invention preferably have a height (h) of 0.3 cm to 1.5 cm, and more preferably a height of 0.5 cm to 1.0 cm.

The forms of administration according to the present invention or, respectively, the strips of material of the strip-shaped forms of administration (1) according to the present invention preferably have a width (b) of 1.0 cm to 12.0 cm, and more preferably a width of 2.0 cm to 6.0 cm.

The forms of administration (1) according to the present invention or, respectively, the strips of material of the strip-shaped forms of administration according to the present invention preferably have a thickness (d) of 10 µm to 500 µm, and more preferably of 20 µm to 300 µm.

Figure 1:
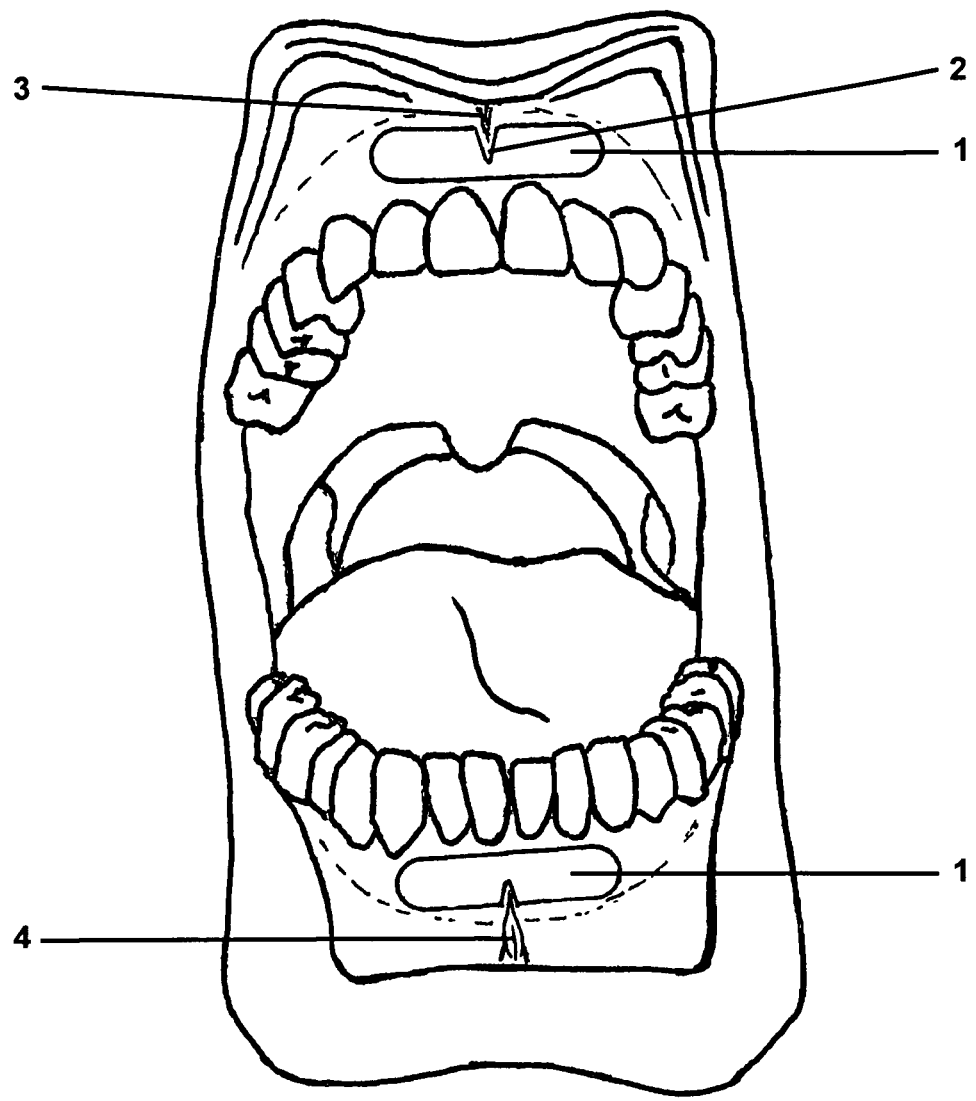
FIG. 1 is a drawing illustrating the correct placement of forms of administration according to the present invention on the upper and lower gums.
Figure 2:
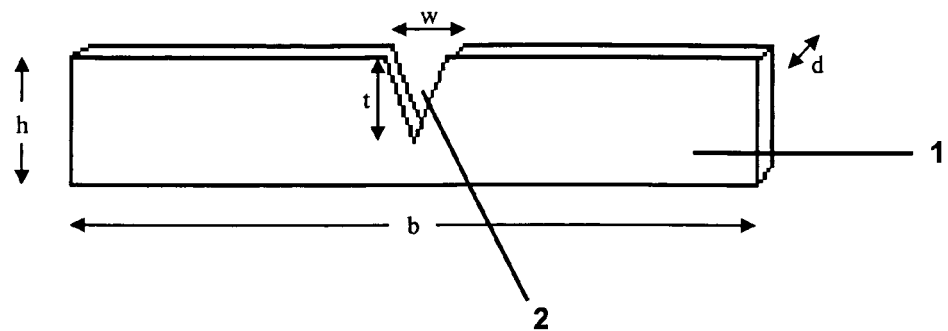
FIGS. 2 A to 2 E show cross-sectional views of various embodiments of the forms of administration according to the present invention.
Figure 2:
Figure 2:
Figure 2:
Figure 2:

The strip-shaped forms of administration (1) of the present invention may have different geometric shapes. Preferably, the form of administration has an arc-shaped contour, an angular contour, a rectilinear contour, or a contour resulting from a combination of the aforementioned contours. Especially preferred geometric shapes are shown in FIGS. 2 A to 2 E.

Figure 3:
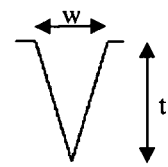
FIGS. 3 A to 3 E show cross-sectional views of various possible configurations of the notch according to the present invention.
Figure 3:
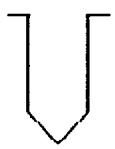
Figure 3:
Figure 3:
Figure 3:

The form of administration (1) according to the present invention has a notch (2) at one of its two longitudinal edges. "Notch" is understood to mean a gap, an incision or cut-out provided in one of the longitudinal edges of the strip of material. The notch (2) located at one of the two longitudinal edges of the strip of material may be of almost any shape. With particular preference, the notch (2) has an arc-shaped contour, an angular contour or a rectilinear contour, or a contour resulting from a combination of the aforementioned contours. The notch may be configured so as to be, for example, wedge-shaped, rectangular, tapered to a point, at least terminally polygonal, or so as to be approximated to an oval or to a circular cut-out. Configurations of the notch (2) which are especially preferred are shown in FIGS. 3 A to 3 E.

The notch (2) preferably has a depth (t) from 2 mm to 13 mm, relative to the point of the notch (2) where the cut is deepest.

In preferred embodiments, the depth of the notch (2) is not less than one-tenth, one-ninth, one-eighth, one-seventh, one-sixth, one-fifth, one-fourth, one-third or one-half of the height (h) of the strip of material.

In preferred embodiments, the depth (t) of the notch (2) does not exceed nine-tenths, eight-ninths, seven-eighths, six-sevenths, five-sixths, four-fifths, three-fourths, two-thirds or one-half of the height (h) of the strip of material.

The notch (2) preferably has a width (w) of 1 mm to 10 mm, referring to its largest width. The largest width of the notch is usually where the edge of the notch meets the longitudinal edge of the strip of material.

In the preferred embodiments, the width of the notch (2) amounts to from one-half to an eight hundred and thirty-third, preferably from one-tenth to one-hundredth, relative to the width (b) of the strip of material.

The notch is dimensioned and arranged such that the frenulum of the upper lip (3) or the frenulum of the lower lip (4) passes through the cut-out if the form of administration is positioned correctly on the gum. The notch ensures that the form of administration can only be used on the gums at the predetermined site, and that this site remains the same even in the case of repeated application, whereby the factors having an influence on the dosage form and thereby on bioavailability always remain unaltered.

The strip-shaped forms of administration (1) according to the present invention may be made of a stiff material or of a flexible material. Numerous materials that are suitable for pharmaceutical and/or cosmetic use by humans and/or in animals, i.e. materials that do not have any unwanted side effects, come into consideration. Unwanted side effects would be toxic effects, the causing of irritations or the triggering of allergic reactions, for example. Suitable materials may be, for example, thermoplastic polymers, thermoset polymers, copolymer films, paper, waxes, textiles (nonwovens, knitted fabrics and woven fabrics), chalks, films, gels and wood composites, as well as combinations of the aforementioned materials.

Specific polymers suitable as material for the strips may be selected from the group of polymers consisting of cellulose ethers, methyl acrylates, hydroxyalkyl celluloses such as hydroxypropyl methyl cellulose, hydroxypropyl cellulose, hydroxyethyl cellulose, methyl cellulose and carboxymethyl cellulose, polysulfones, polyvinyl pyrrolidones, crosslinked polyvinyl pyrrolidones, polyvinyl pyrrolidone-vinyl acetate copolymers, polyvinyl alcohols, polyacrylic acids, polyacrylate polymers, crosslinked polyacrylic acids, polyethylene oxides, polyethylene glycols, polyvinyl alkyl ether-maleic acid imide copolymers and carboxyvinyl polymers.

Suitable polymers may also be selected from the group of polymers consisting of marine colloids, natural gums and polysaccharides. These polymers include, for example, sodium alginate, carrageenan, xanthan gum, gum acacia, gum arabic, guar gum, pullulan, agar, chitin, chitosan, pectin, karaya gum, zein, hordein, gliadin, carob meal, tragacanth and other polysaccharides, starches such as maltodextrins, amylose, amylopectin, maize starch, potato starch, rice starch, tapioca starch, pea starch, sweet potato starch, barley starch, wheat starch, waxy maize starch, modified starch, dextrins, levan, elsinan and gluten; and proteins such as collagen, whey protein, casein, milk protein, soya protein, gelatine, waxes and colophony, as well as synthetic waxes and bees wax.

By combining two or more of the aforementioned polymers, the properties of the strip of material, such as mucoadhesiveness, flexibility, solubility behaviour, swelling behaviour and the like, can be adapted according to one's wishes and requirements.

The strip of material, or the layers of the strip of material, comprise/comprises at least one polymer, which represents an essential component of the strip of material or of the layer(s). The polymer portion amounts to at least 5%-wt. and not more than 90%-wt., preferably 10 to 70%-wt., more preferably 30 to 60%-wt., in each case relative to the strip of material or the layer, respectively.

The strip of material, or individual layers of the strip of material, can furthermore contain excipients or additives in order to control the chemical or physical properties, such as flexibility, mucoadhesive properties, disintegratability, swellability and/or diffusion properties.

To be taken into consideration as excipients or additives are, in particular, substances selected from the group consisting of antioxidants, emulsifiers, gelling agents, flavour enhancers, taste corrigents, flavours, sweeteners, stabilisers, pH regulators, acidifying agents, bulking agents, preservatives, colourings, thickening agents, plasticisers and humectants. Those skilled in the art will know suitable excipients and additives approved for pharmaceutical applications.

Since many active ingredients, especially peptidic medicinal agents, are absorbed only insufficiently through the mucous membranes, addition of so-called enhancers, i.e. substances enabling and/or accelerating absorption, are of great importance.

Enhancers may be selected from the following substances or groups of substances: saturated or unsaturated fatty acids, carbohydrates, straight-chain or branched fatty alcohols, bile salts and bile acid derivatives, cyclodextrins, dimethyl sulfoxide, synthetic and non-ionic emulsifiers, phospholipids, propylene glycol, decanol, dodecanol, 2-octyl dodecanol, glycerine, sorbitol, mannitol and other sugar alcohols, isopropylidene glycerol, transcutol (=diethylene glycol monoethyl ether), DEET (=N,N-diethyl-m-toluene amide), solketal, ethanol, 1-2-propanediol or other alcohols, menthol and other essential oils or components of essential oils, lauric acid diethanolamide, D-alpha-tocopherol and dexpanthenol, chelating agents such as EDTA (ethylene diamine tetraacetic acid); this list is not exhaustive.

The portion of these excipients can preferably amount to from 0.5 to 40%-wt., especially from 1 to 30%-wt., in each case relative to the strip of material or the layer of the strip of material, respectively.

The strip of material can be made of materials that decompose on the gums within a certain period after applying the form of administration to the gum. The forms of administration may release the active ingredient into the oral cavity or to the mucous membrane of the gums before they decompose, and/or the release of the active ingredient may take place after the decomposition of the form of administration. The decomposition of the form of administration can take place in any manner, for example by mechanical, chemical and/or physical stress. Thus, the form of administration may decompose by dissolving, directly or after a chemical reaction. In the case of mechanical stress, this can be, for example, shearing processes or grinding processes. As a physical stress, increased temperature may be mentioned. The forms of administration according to the invention may, for example, disintegrate into small pieces that are visually indiscernible from each other, or an uninterrupted gel layer may form. However, the strip of material can also disintegrate into water-soluble components that dissolve in the saliva during use of the form of administration.

With other embodiments of the forms of administration according to the invention, the strip of material consists of at least one water-insoluble, but decomposable polymer that is dispersible in water. This means that the polymer breaks down into small fragments. The polymer is water-insoluble, but swellable. In other embodiments in which the polymer does not break down during use, the polymer may be a water-repellent polymer or a water-stable hydrophilic polymer, such as certain types of cellulose, for example paper. In some embodiments, the gingival strip may comprise a mixture of film-forming materials.

In the case of water-insoluble strips of material, or in the case of water-insoluble layers in multilayered strips of material, the layer(s) remaining after use have to be removed from the gum after a predetermined period.

The form of administration (1) according to the invention may, in simple embodiments, comprise a single-layer strip of material, but the strip of material may also consist of several layers or plies.

For example, the strip of material may comprise a first layer that comprises a polymer and/or an adhesive, a second layer that comprises an active ingredient or a functional composition, and one or more additional layers that provide further or additional ingredients or impart specific properties to the form of administration.

In a particularly preferred embodiment, one of the outer layers may be mucoadhesive to promote the adherence of the form of administration to the mucous membrane and to facilitate the absorption of active ingredient via the mucous membrane by providing direct contact.

Multilayered strips of material, in particular, may be provided with a marking to ensure that a patient will apply the correct side to the mucous membrane, namely that side through which the active ingredient can be released to the mucous membrane of the gingiva. This marking may be, for example, an imprint in one of the layers, a coloured layer, or other markings.

Water-insoluble layers can be used as protective layers, which prevent the active ingredient from being released into the oral cavity and ensure that the release takes place towards the gingival tissue. Furthermore, the active ingredient can be embedded in a water-insoluble layer, a so-called matrix layer, from which the active ingredient is released by diffusion through pores over a prolonged period of application. Once the active ingredient has been released, the form of administration needs to be removed if it consists of indigestible material.

The strip-shaped forms of administration (1) according to the invention comprise an active ingredient. The active ingredient may be an active pharmaceutical ingredient, i.e. a medicinal agent for therapeutic, prophylactic or diagnostic purposes, or it may be an active cosmetic ingredient.

There are numerous suitable active ingredients the administration of which by a transmucosal form of administration would be advantageous, above all in the group of the analgesics, antiarrhythmics, anti-dementia agents, antidiarrhoeal agents, anti-emetics, anti-epileptics, antihypertensive agents, anti-vertigo agents, corticoids, hormones, cardiacs, coronary agents, migraine analgesics, neuroleptics, psychopharmacological agents, sedatives, etc.

For a gingival absorption, the following active ingredients or, respectively, the derivatives and salts thereof are particularly preferred: alprazolam, apomorphine, acetylsalicylic acid, buprenorphine, captopril, chlorpromazine, codeine, cyanocobalamine, dexamethasone, dextromethorphan, diazepam, diclofenac, diltiazem, domperidone, ergotamine, estradiol, ethynylestradiol, fentanyl, isosorbide dinitrate, levonorgestrel, loperamide, lorazepam, methadone, methylprednisolone, methyltestosterone, metoclopramide, metronidazole, miconazole, morphine, nalbuphine, nifedipine, nicotine, nitroglycerin, norelgestromin, norethisterone acetate, noscapine, olanzapine, omeprazole, oxazepam, oxybutynin, pethidine, prochlorperazine, propranolol, risperidone, rotigotine, testosterone, timolol, verapamil, vitamin $B_{12}$.

Even more preferable would be the parenteral application of peptidic medicinal agents via the oral mucous membrane, above all of proteins having a molecular weight <10 kDa, e.g. calcitonin, desmopressin, GLP-1 analogues, such as exenatide, glucagon, GnRH analogues such as buserelin, insulin and analogues thereof, leu-enkephalin, nafarelin, oxytocin, protirelin, vasopressin and somatostatin analogues such as octreotide. This list is not exhaustive. The form of administration described may in principle be used with any suitable active ingredient.

The strip of material of the forms of administration (1) according to the invention functions as a carrier for the active ingredient. Being a carrier for the active ingredient means any kind of containment of the active ingredient. The active ingredient may be contained, for example, in the form of a dispersion, emulsion or solution, and as a depot in depressions or pockets. However, the strip of material may also be impregnated with a dispersion, emulsion or solution of an active ingredient, or be provided with an active ingredient-containing coating.

Example 1

A mucoadhesive gingival wafer with a monolayered configuration was prepared using the following composition (in percent by weight):

| | |
|---|---|
| Lorazepam | 7.81% |
| Sodium carboxymethyl cellulose 7LF 25 cP | 60.69% |
| Glycerine | 18.0% |
| Beta-cyclodextrin | 10.0% |
| Menthol | 2.5% |
| Sodium saccharinate | 1.0% |

The shape of the individual wafers corresponded to the embodiment shown in FIG. 2C, with a width (b) of 41 mm, a height (h) of 8 mm, a width (w) of the notch of 5 mm, a depth (t) of the notch of 4 mm, and a radius of the lateral curvatures of 4.2 mm. The mass per unit area (dry) was 40 g/m², the thickness (d) 50 μm.

With these dimensions, the area of the wafer was 3.2 cm², and it contained a single dose of lorazepam of 1.0 mg.

Example 2

A gingival wafer having a bilayer configuration was prepared which had a first, water-insoluble layer as protective layer, and a second, mucoadhesive layer which contained active ingredient.

The active ingredient-containing layer is to be applied to the gums, whereas the water-insoluble layer is to reduce the dissolution of the active ingredient in the mouth and thereby reduce the swallowing of the active ingredient. To distinguish the two layers, the mucoadhesive layer was coloured white and the protective layer red.

The protective layer consisted of (in percent by weight):

| | |
|---|---|
| Ethyl cellulose N100 | 50.0% |
| Ethyl cellulose N 50 | 15.0% |
| Miglyol 812 | 34.0% |
| Iron oxide red E | 1.0% |

The protective layer had a mass per unit area (dry) of 45 g/m² and a thickness of 60 μm.

The mucoadhesive layer with the active ingredient propranolol was composed of (in percent by weight):

| | |
|---|---|
| Propranolol HCl | 10.416% |
| Hydroxypropyl methyl cellulose 50 cPs | 73.084% |
| Polyethylene oxide WSR N-10 | 7.0% |
| Glycerine | 7.0% |
| Titanium dioxide | 2.5% |

The layer had a mass per unit area of 150 g/m² and a thickness of 110 μm.

The thickness (d) of the bilayer wafers was 170 μm. The other dimensions of the individual bilayer wafers corresponded to the dimensions indicated in Example 1 for a single-layer embodiment. With a total area of 3.2 cm², the single dose of propranolol was 5.0 mg.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A strip-shaped form of administration or administration form for the transmucosal administration of an active ingredient via the gums, comprising a strip of material having two longitudinal sides each having a frenulum facing edge and an opposite edge when said strip-shaped form is placed in a user's mouth, said strip of material having a notch in the frenulum facing edge for defining a straight angled cut-out for receiving a frenulum of the lip, said strip-shaped form having a height (h) of about 0.5 cm to 1.0 cm to ensure that the administration form can only be used to cover on repeated applications an area of the outer gums above the upper teeth or an area of the outer gums below the lower teeth and not intended to be used on the teeth when a frenulum is received in said notch, and at least one active ingredient, wherein the depth (t) of the notch is not less than one-half of the height (h) of the strip of material relative to the point of the notch where the cut is deepest.

2. The strip-shaped form of administration according to claim 1, wherein said form of administration has a width of 1.0 to 12.0 cm.

3. The strip-shaped form of administration according to claim 1, wherein said form of administration has a thickness of 10 to 500 μm.

4. The strip-shaped form of administration according to claim 1, wherein the notch has a shape selected from the group consisting of wedge-shaped, rectangular, tapered to a point, and at least terminally polygonal.

5. The strip-shaped form of administration according to claim 1, wherein said notch has a width of 1 to 10 mm relative to the widest point of said notch.

6. The strip-shaped form of administration according to claim 1, wherein said notch has a depth of 2 to 13 mm relative to the point where the cut is deepest.

7. The strip-shaped form of administration according to claim 1, wherein the strip of material comprises a flexible material that conforms to the shape of the gums of a user, and wherein the strip of material does not conform to the shape of the teeth of the user.

8. The strip-shaped form of administration according to claim 1, wherein the active ingredient is selected from the group consisting of an active cosmetic ingredient and an active pharmaceutical ingredient.

9. The strip-shaped form of administration according to claim 1, wherein the strip of material is multi-layered.

10. Use of a strip-shaped form of administration according to claim 1 for the transmucosal administration of a medicinal agent via the mucous membrane of the gums.

11. The strip-shaped form of administration according to claim 2, wherein said form of administration has a width of 2.0 to 6.0 cm.

12. The strip-shaped form of administration according to claim 3, wherein said form of administration has a thickness of 20 to 300 μm.

13. A strip-shaped form of administration or administration form for the transmucosal administration of an active ingredient via the gums, comprising a strip of material having two longitudinal sides each having a frenulum facing edge and an opposite edge when said strip-shaped form is placed in a user's mouth, said strip of material having a notch in the frenulum facing edge for defining a straight angled cut-out for receiving a frenulum of the lip, said strip-shaped form having a height (h) of 0.5 cm. to 1.0 cm to ensure that the administration form can only be used to cover on repeated applications an area of the outer gums above the upper teeth or an area of the outer gums below the lower teeth and not intended to be used on the teeth when a frenulum is received in said notch, and at least one active ingredient, wherein said administration form is a non-foldable administration form to prevent either of the longitudinal sides to be substantially bent relative to said frenulum facing edge or said opposite edge.

* * * * *